United States Patent [19]

Leighton et al.

[11] Patent Number: 4,839,809
[45] Date of Patent: Jun. 13, 1989

[54] MAGNETIC PERSONAL TURNING MONITOR

[76] Inventors: Stephen B. Leighton, 93 Jefferson Ave., Maplewood, N.J. 07040; John A. Tenney, 5907 Wood Acres Dr., Bethesda, Md. 20816

[21] Appl. No.: 83,947

[22] Filed: Aug. 4, 1987

[51] Int. Cl.$^4$ .......................... A61B 5/10; G06F 15/42
[52] U.S. Cl. ................................. 364/413.02; 128/782
[58] Field of Search ............ 364/415, 413; 73/178 R; 272/93, DIG. 5, DIG. 6, DIG. 9; 128/782, 2 S, 2 N, 2 R, 653, 665, 777, 782, 774, 776, 731

[56] References Cited

U.S. PATENT DOCUMENTS

| | | | |
|---|---|---|---|
| 3,943,763 | 3/1976 | Garner | 73/178 R |
| 4,197,855 | 4/1980 | Lewin | 364/415 |
| 4,757,453 | 7/1988 | Nasiff | 364/415 |

Primary Examiner—Michael R. Fleming
Attorney, Agent, or Firm—Browdy & Neimark

[57] ABSTRACT

A device for measuring the handedness, left and right, of human ambulatory turning behavior includes a rugged and compact sensing means in the form a Hall-effect compass or flux gate compass, as well as computation and storage and read-out elements for the total number of turns, half turns and quarter turns made by a patient wearing the device.

5 Claims, 1 Drawing Sheet

MAGNETIC PERSONAL TURNING MONITOR

FIELD OF THE INVENTION

The present invention relates to the study and treatment of brain dysfunction and, more particularly, to a device for the measurement and recordation of the turning patterns of neurological and psychiatric patients.

BACKGROUND OF THE INVENTION

Circling behavior is often observed in animals, but it is less well known that this behavior can occur in humans as well. It is often much more subtle in humans. For instance, a human may not necessarily walk monotonously in circles, but he might have a tendency, for example, to turn more to the left or more to the right during the course of otherwise normal movements.

Some research has indicated that this turning behavior can be related to the relative dominance of one half of the brain (cerebral hemisphere) over the other. It may also be related to abnormalities of the brain, and thus a knowledge of the tendency of neurological, or psychiatric patent to turn more frequently in one direction may be helpful in diagnosing that patient. This turning information, when objectively quantified, may also be useful for measuring the effectiveness of certain types of medication.

Circling behavior is for the most part dopaminergically mediated and related to asymmetry in dopaminergic activity between the left and right basal ganglia or left and right frontal cortex. As a rule, animals rotate toward the hemisphere with lower striatal dopaminergic activity. (Bracha, H. S., *Life Sciences,* Vol. 40 pp. 1127–1130) It may give an indication correlated with schizophrenia in human subjects, since schizophrenia is also related to dopaminergic activity. Other reports indicate that turning behavior may also be affected in Parkinsonian patients.

Thus it is desirable to accurately measure the turning tendencies of humans, both for research and potential treatment. It is desirable to be able to record the total number of left turns and of right turns that the patient has made over some time period, say for four or eight hours. In addition, it is desirable to record the total number of left and right half and quarter turns made during the same time period. This latter information is useful, since people make many more of these turns than they make complete 360° turns. If the recorded numbers are larger, the statistical accuracy of the measurement is increased.

An early device (S. D. Glick) was built using a standard hand-held compass consisting of a "needle" pivoted above a card. The position of the needle was sensed by photoelectric cells, and appropriate electronics computed the number of turns in each direction and stored these cumulative totals for later readout by a researcher or physician. This prior device suffered from the following disadvantages: The photoelectric cells required a relatively large electrical power, which limited the measurement time on a given size of battery. The large diameter of the compass made the instrument relatively bulky. The nature of the pivots on such compasses is such that they are relatively sensitive to shocks and thus relatively unreliable. The pivot arrangement of such compasses is also such that they will jam and not turn if the compass is tilted significantly from the normal horizontal position. Since these instruments must be worn on the belt of a patient, they are tilted back and forth most of the time that the patient is walking around, precisely when they should be making an accurate measurement. Power drain was higher, size was larger, and this device was difficult to construct.

Some marine and aircraft compasses could overcome this tilting problem by mounting the compass in a set of gimbals. Such an approach is not practical in this field, because it unduly increases the bulk of the instrument.

SUMMARY OF THE INVENTION

It is, accordingly, an object of the invention to overcome deficiencies in the prior art, such as indicated above.

It is another object to provide improvements in the treatment and study of brain dysfunction.

It is a further object to measure and record turning behavior in a more effective way.

It is yet another object to provide an improved personal turning monitor which works on magnetic principles and which can be easily and inconspicuously worn by a patient.

It is still another object to provide a suitable instrument for measuring the turning tendencies of a human which will record the total number of left turns and of rights turns that the person wearing the instrument has made over some time period, and which will record the total number of left and right half and quarter turns made during the same term.

It is another object to provide such an instrument which is compact and lightweight so that a patient will not object to or be burdened by wearing it, and which is sufficiently rugged so that it can withstand the abuse to which some mental patients will subject it, and which is reliable and accurate so that the data it produces can be trusted to truly represent the movements of the patient.

It is still another object to provide such an instrument which is unobtrusively wearable by a patient during his or her normal activities so that the patient will be less conscious of its presence and therefore less likely to purposefully interfere with the measurements being taken, such an instrument being able to function almost anywhere a patient might travel.

It is still another object to provide such an instrument which relies for an orientation reference on the earth's magnetic field, and which is sensed in a simple way by the principle of a magnetic compass.

The present invention thus involves a compass means for generating electronic signals that are determined by the direction that the device is pointed relative to the earth's magnetic field; and a means for comparing successive signals and thus computing which direction the case of the device is being turned; and a means for summing or totalizing the number of turns, half turns, and/or quarter turns, both clockwise and counterclockwise independently; and a means for displaying these totals, and a means for resetting the totals. The compass means consists of either (A) a piece of magnetic material physically pivoted with respect to the case such that it can remain oriented with respect to the earth's magnetic field, with four Hall effect devices arrayed around the material, such that one or two Hall devices are active when the magnetic material is oriented near them, or (B) a flux gate type compass, of which several designs are known.

The Hall effect compass, or the flux gate compass, makes the entire instrument practical. They are rugged, compact and much less subject to jamming or tilting then other types of compasses. In addition, they use much less power than the photoelectric designs. Thus, with regard to the closest previously known device, i.e. of S. D. Glick as mentioned above, the present invention works better in that it is more accurate, is less expensive, is more rugged, runs longer on a set of batteries as there is less of a power drain, is smaller and more compact and thus more convenient to use, and receives better patient acceptance.

BRIEF DESCRIPTION OF DRAWING

The invention as well as other objects and advantages will be more apparent from the following detailed description of embodiments taken in conjunction with the drawings, wherein.

DETAILED DESCRIPTION OF PREFERRED EMBODIMENTS

Figure 1:
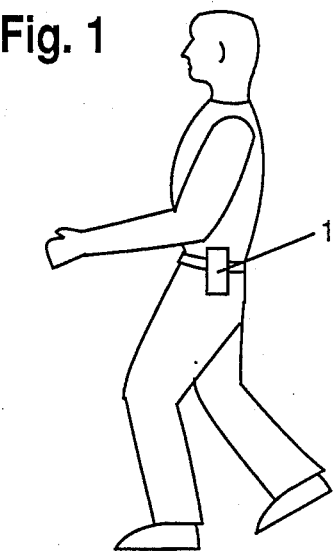
FIG. 1 shows the belt-mounted unit being worn by a patient.

FIG. 1 shows a patient with the device of the present invention in a cover 1 which may be suitably suspended on a belt around the waist. If desired, and as preferred, the cover 1 can be provided with a lock so as to prevent patient tampering.

Figure 2:
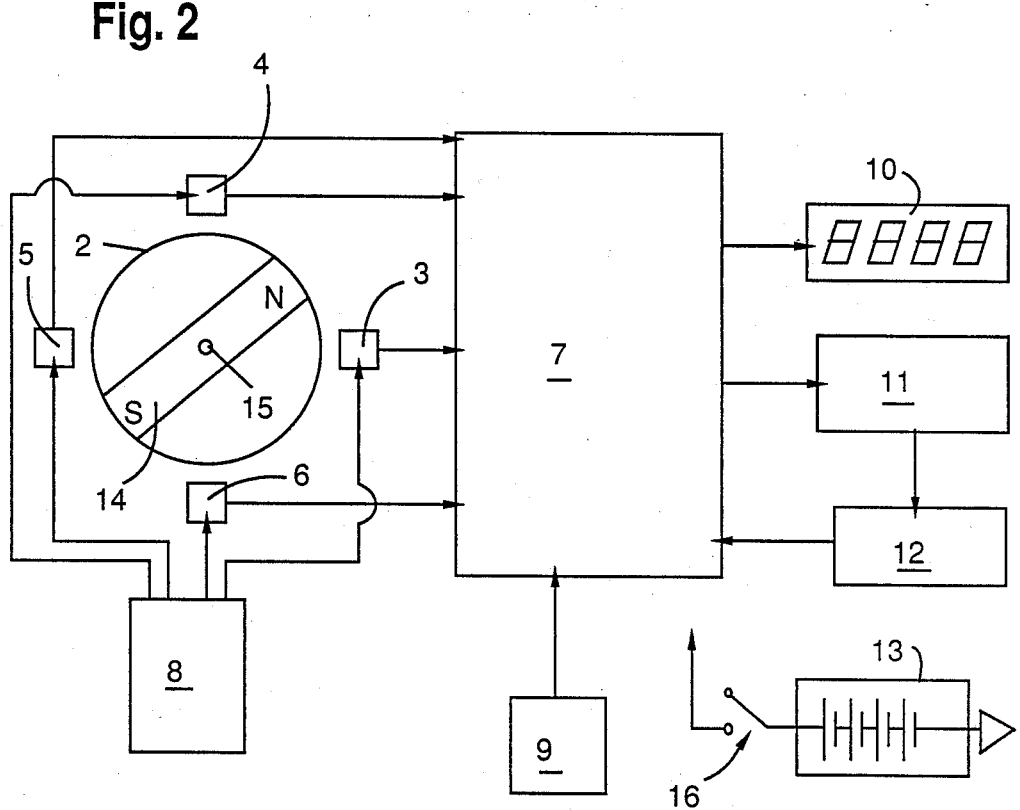
FIG. 2 is a schematic diagram of one embodiment.

In FIG. 2, a small piece of magnetic material 14 is mounted on a pivot 15 in a case 2. The magnetic material remains oriented with the earth's magnetic field, and the case and all other parts turn with the patient. Four Hall-effect sensors 3, 4, 5, 6 are mounted on the periphery of the case 2. These are wellknown commercial semiconductor devices that are sensitive to magnetic fields. When the "North" pole of the material 14 is close to one of the sensors, and when the device is turned on so that all the sensors are activated by an electronic driver circuit 8, that sensor puts out an electrical signal to a microcomputer 7.

Figure 3:
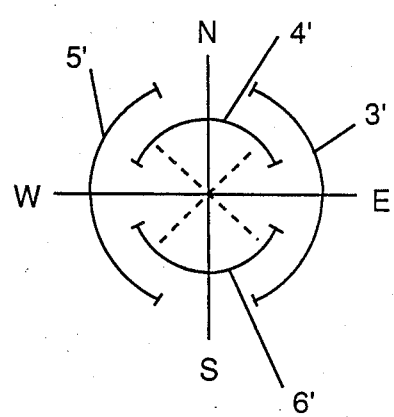
FIG. 3 is a schematic representation of the response angles of each of the four sensors.

The arrangement of the sensors is such that their sensitive fields overlap as schematically shown in FIG. 3. For example, if the "North" pole of the material 14 is oriented anywhere in the directions labeled 4', then sensor 4 will be activated, and so on. Thus four sensors can indicate eight directions. Sensor 4 alone indicates "North". Sensors 4 and 3 at the same time indicate "Northeast". Sensor 3 alone indicates "East", and so on.

The microcomputer 7 activates the driver 8 often enough not to miss any turns, but keeps it turned off much of the time to reduce power consumption. The computer 7 keeps track of successive states of the sensors so that it can compute the direction and amount of turning. For example, if first sensor 3 is active, then sensors 3 and 6, then sensor 6 alone, then sensors 6 and 5, then sensor 5 alone, a left handed one half turn has been made by the person wearing the device. This fact is totalized in the computer memory.

A control switch 9 is provided to cause the computer to display the totals in a display 10. A battery pack 13 has a switch 16 which resets the totals to zero. A program address latch 11 and a program memory 12 are provided, it being understood that the microcomputer 7, the program address latch 11 and the program memory 12 comprise typical microcomputer system components which can be routinely implemented in many different ways. Alternatively, the computer can be replaced by hard wired electronics such as a gate array.

A flux-gate compass has been described in U.S. Pat. No. 3,943,763, and in many other references. Such a compass can be used to substitute for the moving magnetic material and Hall-effect array. The rest of the system remains the same. A small amount of simple interfacing logic is provided to adapt the output signal of the flux gate compass to the microcomputer.

A timing mechanism may also be added to record the various types of turns during various time periods, such as 15 minutes, one hour, etc. The added feature of a timer allows one to further distinguish among different types of turning behaviors.

Devices according to the present invention have been made and tested with success. In its presently embodied form, the preferred turning monitor of the present invention is of the size of a pocket calculator and contains the magnetic compass as shown in FIG. 2 with Hall-effect transducers, the microprocessor, batteries and appropriate interface and display and control circuits. It counts, records and displays the number of right and left 90°, 180° and 360° turns made by the wearer since the last reset. The counts are stored until a switch is thrown to display them on a small alphanumeric LED display 10, after which the device may be reset or not. This device has been tested to collect patient data from schizophrenic patients undergoing various drug regimens and is being further tested to detect lateralization effects associated with these conditions (Bracha et al, in press).

It will be obvious to those skilled in the art that various other changes and modifications may be made without departing from the scope of the invention and the invention is not to be considered limited to what is shown in the drawings and described in the specification.

What is claimed is:

1. A magnetic personal turning monitor comprising compass means for generating electronic signals which are determined by the direction that said monitor is pointed relative to the earth's magnetic field;

signal comparing means for comparing successive signals and computing which direction said device is being turned;

summing means for totalizing the number of turns, half turns and quarter turns both clockwise and counterclockwise independently; means for displaying the totals of said turns; and means for resetting said signal comparing means and summing means.

2. A device according to claim 1 wherein said compass means comprises a magnetic needle physically pivoted with respect to said case and four equally spaced Hall-effect devices arrayed around said magnetic neeedle.

3. A device according to claim 1 wherein said compass means comprises a flux gate type compass.

4. A device according to claim 1 wherein said compass means comprises means for generating said electronic signals without jamming and at low power consumption.

5. A device according to claim 4, wherein said compass means is rugged and compact.

* * * * *